(12) United States Patent
Chitturi et al.

(10) Patent No.: US 6,433,225 B1
(45) Date of Patent: Aug. 13, 2002

(54) PROCESS FOR THE PREPARATION OF FLUVOXAZMINE MALEATE

(75) Inventors: Trinadha Rao Chitturi; Rajamannar Thennati; Kanaksinh Jesingbhai Jadav; Hemant Ashvinbhai Shah, all of Baroda (IN)

(73) Assignee: Sun Pharamaceutical Industries, Ltd., Mumbai (IN)

( * ) Notice: Subject to any disclaimer, the term of this patent is extended or adjusted under 35 U.S.C. 154(b) by 21 days.

(21) Appl. No.: 09/696,613

(22) Filed: Oct. 25, 2000

(30) Foreign Application Priority Data

Nov. 12, 1999 (IN) ........................... 796/BOM/99

(51) Int. Cl.[7] ............................. C07C 249/12
(52) U.S. Cl. ......................... 564/256; 564/262
(58) Field of Search ................... 564/256, 262

(56) References Cited

U.S. PATENT DOCUMENTS 4,085,225 A   4/1978   Welle et al. .................. 424/304

OTHER PUBLICATIONS

Database CAPLUS on STN, Acc. No. 1977:72203, 'Substituted 4'–trifluoromethylvalerophenone O–(2–aminoethyl)oxime derivatives with antidepressive action.' NL 7503310 (abstract).*

Database CAPLUS on STN, Acc. No. 1982:562585, Welle et al., 'Oxime ether compounds.' CH 629761 (abstract).*

Database CAPLUS on STN, Acc. No. 1997:403525, Matarrese et al., 'Synthesis of [O–methyl–11–C]fluvoxamine—a potential serotonin uptake site radioligand.' Appl. Radiat. Isot. (1997), 48(6), pp. 749–754 (abstract).*

* cited by examiner

Primary Examiner—Brian J. Davis
(74) Attorney, Agent, or Firm—Ladas & Parry

(57) ABSTRACT

A process is described for the preparation of substantially pure fluvoxamine maleate, an important antidepressant drug of the formula I, for use as an active pharmaceutical ingredient (API), from the corresponding oxime viz 5-methoxy-4'-trifluoromethylvalerophenone oxime of formula II.

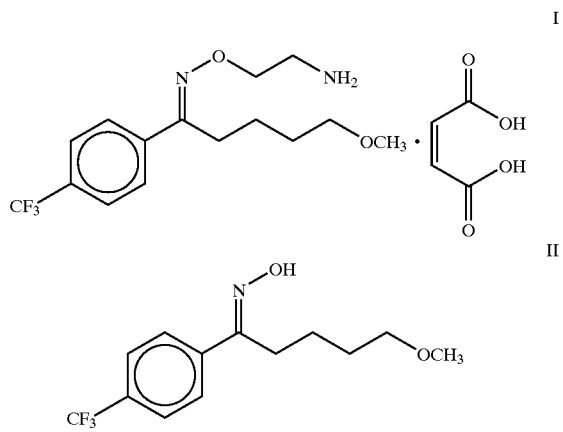

20 Claims, No Drawings

PROCESS FOR THE PREPARATION OF FLUVOXAZMINE MALEATE

The present invention relates to a process for the preparation of maleate salt of 5-methoxy-1-[4'-(trifluoromethyl)phenyl]-1-pentanone O-(2-aminoethyl)oxime viz fluvoxamine maleate in a substantially pure form. Fluvoxamine maleate is an important drug used in the treatment of depression.

BACKGROUND OF THE INVENTION

U.S. Pat. No. 4,085,225 discloses the process for the preparation of fluvoxamine maleate, a compound of formula I, by alkylation reaction of 5-methoxy-4'-trifluoromethylvalerophenone oxime, a compound of formula II, with 2-chloroethylamine hydrochloride in dimethylformamide in the presence of a base viz. potassium hydroxide for two days at 25° C.

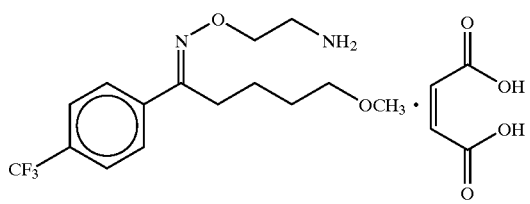

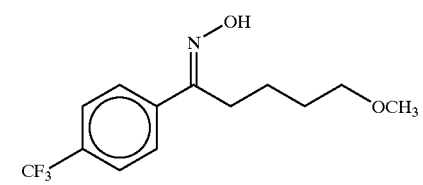

Subsequently the solvent is removed under vacuum then the residue is acidified and extracted with ether to remove the unreacted oxime. The fluvoxamine base is then obtained by extraction into ether after basification, and the ether extract is washed with NaHCO$_3$ solution. The fluvoxamine base is then treated with maleic acid in ethanol, and the residue obtained by concentration under vacuum is recrystallised from acetonitrile to obtain fluvoxamine maleate I. This process when attempted by us was found to be very time consuming. Moreover, the requirement of various solvents posed the problem of their recovery and re-usability.

In an alternate route described in the above mentioned patent, the oxime II is converted to I in a five step process viz., alkylation of II with ethylene oxide to give the hydroxyethyl compound III, which is converted to a mesylate derivative IV with methanesulfonyl chloride and triethylamine, and then aminated with ammonia to give fluvoxamine base.

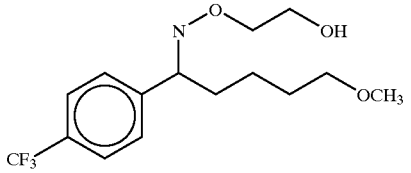

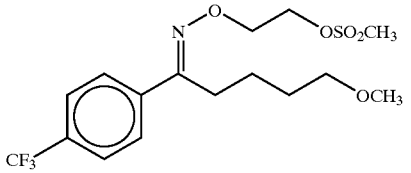

The base is then converted to the maleate salt I, which is finally purified by recrystallization from acetonitrile.

Although in principle, the process described gives the desired product, viz. fluvoxamine maleate I, it was not found to be attractive as it involves a number of unit operations, use of several solvents, and handling of toxic and explosive ethylene oxide, a potential carcinogen. The number of operations used result in long occupancy of reactors and utilities, and high-energy consumption making it a commercially unviable process on a large scale. Also, for large-scale operations, the use of several different solvents in the process poses ecological and other usual problems such as storage, their recovery and re-usability. Furthermore, purification of the intermediate III requires cumbersome technique viz. chromatography over silica gel.

The lengthy work-up procedure in U.S. Pat. No. 4,085,225 requires complete removal of organic solvents at different stages; a simple and efficient process has been found wherein:

(a) the alkylation reaction could occur very rapidly in a water immiscible inert aprotic solvent in the presence of a facilitator;

(b) the unwanted reaction components i.e. the excess base, salts and the added facilitator could be easily removed in one step by washing the reaction mixture with water;

(c) the organic layer containing fluvoxamine base treated with maleic acid; and (d) the fluvoxamine maleate obtained in a substantially pure form by recrystallization.

OBJECT OF THE INVENTION

It is thus an object of the present invention to provide a simple process for the preparation of fluvomaxine maleate I comprising of minimum number of unit operations and solvents, and the fluvoxamine maleate I produced is in a substantially pure form.

It is further object of the present invention to provide a process for the preparation of fluvomaxine maleate I by the use of a single water immiscible aprotic solvent in the presence of facilitator coupled with washing the reaction mixture with water such that the process requires very short reaction time and avoids an elaborate work-up procedure using several different solvents and a number of unit operations.

It is still further object of the present invention to provide a process for the preparation of fluvomaxine maleate I which essentially uses a single major aprotic organic solvent, which can be almost quantitatively recovered and re-used thus making the process cost-effective.

It is yet another object of the present invention to provide a process for the preparation of fluvomaxine maleate I in which a plurality of steps are carried out in a single reactor during commercial production to achieve efficiency and economy.

It is still further object of the present invention to provide a process for the preparation of fluvomaxine maleate I which conforms to British Pharmacopoeial specifications (British Pharmacopoeia, 1999, Vol I, British Pharmacopoeia Commission, HMSO Publication, London).

SUMMARY OF THE INVENTION

Thus the present invention relates to a simple and efficient process for the preparation of fluvoxamine maleate of formula I in a substantially pure form:

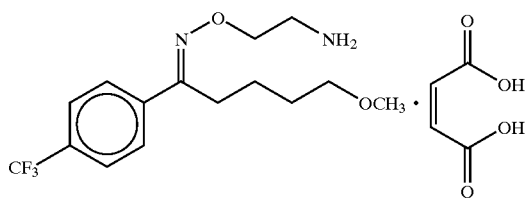

The process comprising
a) reacting of oxime of formula II

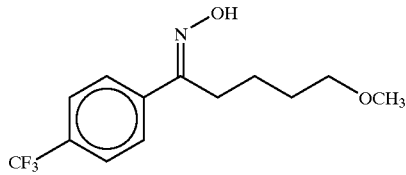

with 2-chloroethylamine hydrochloride, in presence of a base and a facilitator in a water immiscible inert aprotic solvent;
b) washing the reaction mixture with water;
c) treating the organic layer containing fluvoxamine base with a solution of maleic acid in a protic solvent or water to obtain fluvoxamine maleate; and
d) recrystallising the fluvoxamine maleate thus obtained.

For the purpose of maleate salt formation in situ, due to the limitations of the solubility of maleic acid, its addition as a solution was studied in protic solvents and in water. In both the cases fluvoxamine maleate free from contaminants crystallized out, and could very easily be separated out by filtration, thus obviating many operations such as concentrations, extractions etc., and the use of several different solvents.

DETAILED DESCRIPTION OF THE INVENTION

According to the process of the present invention, the oxime II is reacted with 2-chloroethylamine hydrochloride in the presence of a base. Examples of bases that may be used in the process of the present invention include an alkali metal alkoxide of $C_1$ to $C_5$ alcohols; an alkali metal hydroxide such as LiOH, NaOH, KOH, CsOH; and an alkali metal carbonate such as $Li_2CO_3$, $Na_2CO_3$, $K_2CO_3$, $Cs_2CO_3$. The bases that can preferably be employed are alkali metal hydroxides such as LiOH, NaOH, KOH, CsOH; most preferred being KOH. About 1 to 10 moles of base are used for one mole of oxime II. More preferably 4 to 5 moles of base are used for one mole of oxime II.

According to the process of the present invention, the oxime II is reacted with 2-chloroethylamine hydrochloride in the presence of a base in a water immiscible inert aprotic solvent. Examples of water immiscible inert aprotic solvents that may be used include ethers such as diethyl ether, diisopropyl ether, tert-butyl methyl ether, aliphatic hydrocarbons with $C_5$ to $C_{10}$ carbons, which may be branched or linear, and aromatic hydrocarbon solvents such as benzene, toluene, or xylenes.

Preferably the solvent is selected from aromatic hydrocarbons such as toluene and xylenes. More preferably the solvent is toluene.

The rate of base mediated alkylation reaction of the oxime II, with 2-chloroethylamine hydrochloride to produce fluvoxamine base, in a water immiscible inert aprotic solvent, is enhanced in the presence of a facilitator such that substantially pure fluvoxamine maleate is easily prepared, in situ, by the addition of a solution of maleic acid in aprotic solvent, and subsequent recrystallization. The facilitator is selected from a substance that has the property to complex or solvate metal cations, for example, a polyether. Alternatively, the facilitator can be selected from substances that can exchange the metal cations with hydrophobic cations, for example, a quaternary ammonium salt or a quaternary ammonium hydroxide where substituents on the nitrogen are selected from alkyl or aralkyl groups, for example, benzyltrialkylammonium halide.

The polyether is preferably a cyclic polyether such as a crown ether or an acyclic polyether such as a poly(alkylene) glycol.

The poly(alkylene) glycol is preferably a poly(ethylene) glycol (PEG) and more preferably a poly(ethylene) glycol with an average molecular weight in the range between 200 to 10,000. Most preferably the poly(alkylene) glycol is a poly(ethylene) glycol (PEG) with an average molecular weight in the range between 200 to 1000.

The temperature at which the reaction between oxime II and 2-chloroethylamine hydrochloride is carried out ranges from 0° C. to 140° C., preferably between about 20° C. to 60° C. The selection of the temperature depends on the reaction mixture composition and particularly on the solvent and the facilitator used in the process.

In a preferred embodiment of the invention the process of the present invention is carried out in an aromatic hydrocarbon solvent in presence of alkali metal hydroxide as base, poly(ethylene) glycol with molecular weight 200 to 1000 as a facilitator at temperature between 20° C. to 60° C.

In a still preferred embodiment of the invention the process of the present invention is carried out in toluene in presence of KOH and poly(ethylene) glycol with molecular weight 400, at temperature between 30° C. to 40° C.

In a further preferred embodiment of the invention the process of the present invention is carried out in toluene in presence of KOH and poly(ethylene) glycol with molecular weight 400, at temperature between 30° C. to 40° C.; the mole ratio of KOH with respect to oxime is 4 to 5:1.

Upon completion of the reaction, water is added and the organic layer is separated. The organic layer containing fluvoxamine base is treated with a solution of maleic acid in water or a protic solvent, whereby the maleate salt of fluvoxamine crystallizes out.

Preferably solution of maleic acid in water or protic solvent selected from $C_1$ to $C_5$ alcohol like methanol or ethanol is used. Most preferably a solution of maleic acid in water is used.

The salt produced is purified by a simple step of recrystallization from a suitable solvent, preferably water, 2 to 6 volumes, preferably 3 volumes, to directly obtain substantially pure fluvoxamine maleate.

The principal advantage of the process of the present invention is that it is fast with a simple work-up procedure saving on time, solvents and energy consumption as a result. The process is cost-effective and suitable for scale-up on commercial basis.

The following examples illustrate the invention but do not limit the scope of the invention.

EXAMPLE 1

To a stirred mixture of toluene (1.20 lit.), PEG-400 (0.4 lit) and powdered potassium hydroxide (86.0 g on 100% basis, 1.53 mol.) at ambient temperature is added 5-methoxy-4'-trifluoromethylvalerophenone oxime (100 g, 0.363 mol.), followed by 2-chloroethyl amine hydrochloride (50.56 g, 0.435 mol.). The mixture is stirred at 30–35° C. for 2 hours. Water (1.2 lit.) is then added, stirred for 30 mins. and the aqueous layer is separated out. The organic layer is washed with water (~3×500 ml) until the washings are neutral. To the washed organic layer is added a solution of maleic acid (14.14 g, 0.363 mol.) in water (65 ml) and the mixture is stirred at 25–30° C. temperature for 2 hours, then cooled to 5–10° C. when the maleate salt crystallizes out. The crystallized fluvoxamine maleate is filtered, washed with toluene (200 ml) and sucked to dryness. The crude fluvoxamine maleate thus obtained is dissolved in water (300 ml) at 50–55° C. to get a clear solution, then gradually cooled to 5–8° C. and then further stirred at this temperature for 2 hours. The recrystallised fluvoxamine maleate is filtered, washed with chilled water (5° C., 100 ml) and sucked dry. The product is finally dried at 50–55° C. to constant weight. The fluvoxamine maleate obtained complies with the specifications of British Pharmacopoeia, 1999.

EXAMPLE 2

This process when scaled up in pilot plant on 4.0 kg scale input of 5-methoxy-4'-trifluoromethylvalerophenone oxime gave 4.5 kg (71.2%) of fluvoxamine maleate, complying to the specifications of British Pharmacopoeia, 1999.

What is claimed is:

1. A process for the preparation of fluvoxamine maleate of formula I

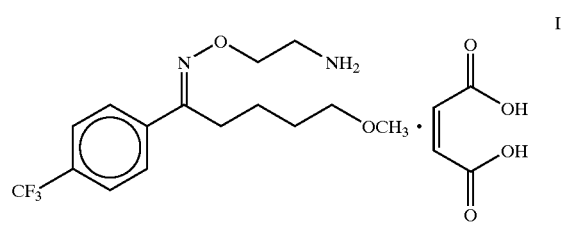

comprising the steps of:
a) reacting oxime of formula II

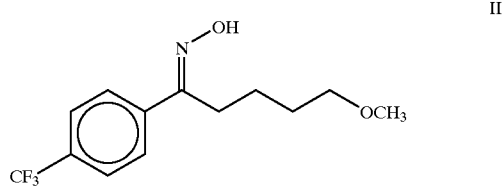

with 2-chloroethylamine hydrochloride, in the presence of a base and a facilitator in a water immiscible inert aprotic solvent;
b) washing the reaction mixture with water;
c) treating the organic layer containing fluvoxamine base with a solution of maleic acid in a protic solvent or water to obtain fluvoxamine maleate; and
d) recrystallizing the fluvoxamine maleate.

2. A process according to claim 1, wherein the base is selected from an alkali metal alkoxide of $C_1$ to $C_5$ alcohols, an alkali metal hydroxide or an alkali metal carbonate.

3. The process according to claim 1, wherein the mole ratio of base to the oxime is 1 to 10:1.

4. The process according to claim 1, wherein the mole ratio of base to the oxime is 4 to 5:1.

5. The process according to claim 2, wherein the base is an alkali metal hydroxide.

6. The process according claim 5, wherein the base is KOH.

7. The process according to claim 1 wherein the base is KOH and the mole ratio of KOH to the oxime II is 4 to 5:1.

8. The process according to claim 1, wherein the water immiscible inert aprotic solvent is selected from an ether, a $C_5$–$C_{10}$ aliphatic hydrocarbon or an aromatic hydrocarbon.

9. The process according to claim 8, wherein the water immiscible inert aprotic solvent is an aromatic hydrocarbon.

10. The process according to claim 9, wherein the solvent is toluene.

11. The process according to claim 1, wherein the facilitator is a polyether.

12. The process according to claim 11, wherein the polyether is a cyclic polyether or an acyclic polyether.

13. The process according to claim 12, wherein the cyclic polyether is a crown ether.

14. The process according to claim 12, wherein the acyclic polyether is a poly(alkylene)glycol.

15. The process according to claim 14, whrein the poly(alkylene) glycol is selected from a poly(ethylene) glycol (PEG).

16. The process according to claim 1, wherein the facilitator is a quatemary ammonium salt or a quatenary ammonium hydroxide where the substituents on the nitrogen are alkyl or aralkyl.

17. The process according to claim 1, wherein the base is an alkali metal hydroxide; the water immiscible inert aprotic solvent is an aromatic hydrocarbon solvent; the facilitator is a poly(ethylene) glycol (PEG) with molecular weight 200 to 1000 and the reaction is carried out at a temperature between 20° C. to 60° C.

18. The process according to claim 1, wherein the base is KOH, the mole ratio of KOH to oxime is 4 to 5:1; the water immiscible inert aprotic solvent is toluene; the facilitator is a poly(ethylene) glycol (PEG) with molecular weight 400 and the reaction is carried out at a temperature between 30° C. to 40° C.

19. The process according to claim 1, wherein the organic layer containing fluvoxamine base is treated with a solution of maleic acid in a protic solvent selected from $C_1$ to $C_5$ alcohol or water.

20. The process according to claim 1, wherein the fluvoxamine maleate is purified by recrystallization from water.

* * * * *

UNITED STATES PATENT AND TRADEMARK OFFICE
CERTIFICATE OF CORRECTION

PATENT NO. : 6,433,225 B1  
DATED : August 13, 2002  
INVENTOR(S) : Trinadha Rao Chitturi et al.

It is certified that error appears in the above-identified patent and that said Letters Patent is hereby corrected as shown below:

<u>Title page, Item [54] and Column 1, line 4,</u>
"FLUVOXAZMINE" should read -- FLUVOXAMINE --
Item [73], "Pharamaceutical" should read -- Pharmaceutical --.

Signed and Sealed this

Third Day of December, 2002

JAMES E. ROGAN
*Director of the United States Patent and Trademark Office*